United States Patent [19]

Daumiller et al.

[11] 4,085,269

[45] Apr. 18, 1978

[54] 1,3,5 TRIS-(2-CHLOROFORMYL-OXYETHYL)-ISOCYANURATE

[75] Inventors: Guenther Daumiller, Heidelberg; Karl Merkel, Ludwigshafen; Franz Neumayr, Weisenheim; Kurt Schneider, Bad Durkheim, all of Germany

[73] Assignee: BASF Aktiengesellschaft, Ludwigshafen, Germany

[21] Appl. No.: 810,274

[22] Filed: Jun. 27, 1977

[30] Foreign Application Priority Data

Jul. 27, 1976 Germany ............................. 2633685

[51] Int. Cl.$^2$ ......................................... C07D 251/34
[52] U.S. Cl. ..................................................... 544/221
[58] Field of Search ......................................... 544/221

[56] References Cited

U.S. PATENT DOCUMENTS 3,697,584  10/1972  Little ..................... 544/221

Primary Examiner—John M. Ford
Attorney, Agent, or Firm—Keil, Thompson & Shurtleff

[57] ABSTRACT

A new compound, 1,3,5-tris-(2-chloroformyl-oxyethyl)-isocyanurate.

1 Claim, No Drawings

1,3,5 TRIS-(2-CHLOROFORMYL-OXYETHYL)-ISOCYANURATE

The present invention relates to a new compound, 1,3,5-tris-(2-chloroformyl-oxyethyl)-isocyanurate (I), which may be obtained from tris-(hydroxyethyl)-isocyanurate in accordance with the following equation:

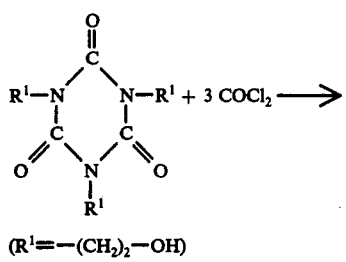

($R^1 = -(CH_2)_2-OH$)

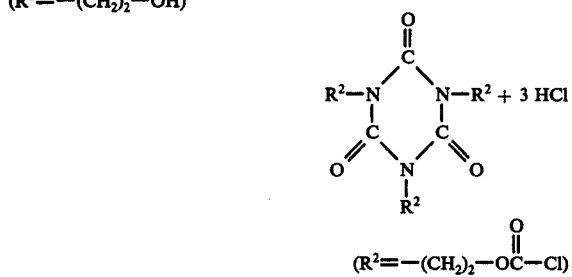

($R^2 = -(CH_2)_2-O\overset{O}{\underset{\|}{C}}-Cl$)

Tris-(hydroxyethyl)-isocyanurate is manufactured by adduct formation between ethylene oxide and cyanuric acid and is a conventional commercial product offered, for example under the trademark "THEIC", for the manufacture of heat-resistant surface coatings, and for use as a crosslinking agent.

The tris-chlorocarbonate or tris-chloroformate of the invention has a melting point of 71° C and is an interesting intermediate which may be used for further reactions, eg. with alcohols to give the corresponding carbonate esters, especially with unsaturated alcohols to give polymerizable carbonate esters, and with amines to give urethanes and polyurethanes, and which imparts valuable properties to the compounds manufactured therewith. These interesting properties in particular concern heat resistance.

MANUFACTURING EXAMPLE 4,000 kg of 1,4-dioxane, to serve as the solvent, are introduced into a stirred production vessel. 1,400 kg of tris-(hydroxyethyl)isocyanurate are dissolved therein, whilst stirring, and 1,760 kg of phosgene are then passed in at 30° C over 3 hours. The mixture is stirred for a further 2 hours. After completion of the reaction, the excess phosgene and the solvent are driven off. The residue obtained consists of 2,452 kg of moist tris-(2-chloroformyl-oxyethyl)-isocyanurate, corresponding to 102% of the calculated amount. It is to be assumed that small amounts of (residual) dioxane distort the fact that the reaction is inherently quantitative. The product has a melting point of 71° C and is pale yellow to colorless, its color number on the iodine scale being from 2 to 4. The calculated chlorine content is 23.7%, and the found content 23.3%. The calculated nitrogen content is 9.4%, and the found content 9.3%. The product is, even in this condition, sufficiently pure for further reactions, eg. with alcohols and amines.

USE EXAMPLE

Manufacture of tris-(2-allyl-oxycarbonyl-oxyethyl)-isocyanurate (II)

The compound II

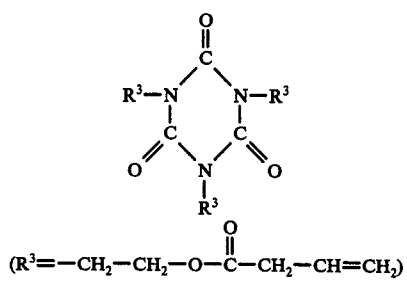

($R^3 = -CH_2-CH_2-O-\overset{O}{\underset{\|}{C}}-CH_2-CH=CH_2$)

is manufactured by reacting (I) with allyl alcohol, as follows:

896 parts by weight of tris-(2-chloroformyl-oxyethyl)-isocyanurate are introduced into a stirred vessel fitted with an off-gas line. 370 parts by weight of allyl alcohol are run in over 5 hours at from 90° to 100° C internal temperature, whilst stirring, and the mixture is then stirred for a further 3 hours at from 80° to 90° C. During the addition of the allyl alcohol, 218 parts by weight of HCl gas are evolved. 1,028 parts by weight of (II) are obtained.

The compound (II) may be used for the manufacture of a highly heat-resistant surface coating, by conventional methods.

We claim:

1. Tris-(2-chloroformyl-oxyethyl)-isocyanurate of the formula

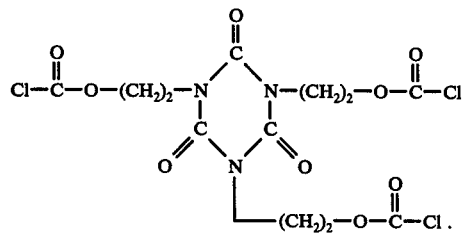

* * * * *